United States Patent
Vu et al.

(10) Patent No.: US 9,474,956 B2
(45) Date of Patent: Oct. 25, 2016

(54) METHODS AND SYSTEMS FOR DISPLAYING REPRESENTATIONS OF FACIAL EXPRESSIONS AND ACTIVITY INDICATORS ON DEVICES

(71) Applicant: Misfit Wearables Corporation, Salem, NH (US)

(72) Inventors: Sonny Vu, Salem, NH (US); Jessica Sheung-yan Ng, San Francisco, CA (US); Matthew Ryan Montgomery, Palo Alto, CA (US)

(73) Assignee: MISFIT, INC., Burlingame, CA (US)

( * ) Notice: Subject to any disclaimer, the term of this patent is extended or adjusted under 35 U.S.C. 154(b) by 0 days.

(21) Appl. No.: 14/336,064

(22) Filed: Jul. 21, 2014

(65) Prior Publication Data

US 2015/0022366 A1 Jan. 22, 2015

Related U.S. Application Data

(60) Provisional application No. 61/857,016, filed on Jul. 22, 2013.

(51) Int. Cl.
*A63B 71/06* (2006.01)

(52) U.S. Cl.
CPC .... *A63B 71/0622* (2013.01); *A63B 2071/0658* (2013.01); *A63B 2220/12* (2013.01); *A63B 2220/17* (2013.01); *A63B 2220/20* (2013.01); *A63B 2220/30* (2013.01); *A63B 2220/40* (2013.01); *A63B 2220/73* (2013.01); *A63B 2225/20* (2013.01); *A63B 2225/50* (2013.01); *A63B 2230/06* (2013.01);

(Continued)

(58) Field of Classification Search
CPC ... A61B 5/1118; A61B 5/1176; A63B 24/00; A63B 71/0622; A63B 2220/17; A63B 2220/20; A63B 2220/40; A63B 2230/06; A63B 2230/01; G06F 19/3481; G01C 21/20; G08B 21/24
USPC ................ 340/539.1, 539.11, 539.12, 573.1, 340/573.4, 691.6; 700/91, 92, 108
See application file for complete search history.

(56) References Cited

U.S. PATENT DOCUMENTS 6,239,787 B1   5/2001  Sugaya
6,802,757 B1  10/2004  Sejnowski (Continued)

FOREIGN PATENT DOCUMENTS

| CN | 101054074 | 10/2007 |
|---|---|---|
| WO | WO2006105094 | 10/2006 |
| WO | WO2013058934 | 4/2013 |

OTHER PUBLICATIONS

International Search Report and Written Opinion for PCT/US2014/047367, mailed Nov. 24, 2014, 16 pages.

*Primary Examiner* — Hung T Nguyen

(57) ABSTRACT

A method for displaying representations of facial expressions on devices includes receiving, by a processor on a device, data from a sensor coupled to the device. The method includes identifying, by the processor, responsive to the received data, a level of progress that a user of the device made towards a goal. The method includes selecting, by the processor, responsive to the identification, an icon representing a facial expression. The method includes modifying, by the processor, a level of power for each of a plurality of light indicators embedded in the device to display the icon.

17 Claims, 16 Drawing Sheets

(52) U.S. Cl.
CPC ....... *A63B 2230/10* (2013.01); *A63B 2230/30* (2013.01); *A63B 2230/60* (2013.01)

(56) References Cited

U.S. PATENT DOCUMENTS

| | | |
|---|---|---|
| 2010/0310157 A1 | 12/2010 | Kim et al. |
| 2011/0095916 A1 | 4/2011 | Kass et al. |
| 2011/0140931 A1 | 6/2011 | Geurts et al. |
| 2011/0242344 A1* | 10/2011 | Elwell ..................... G06F 3/017 348/222.1 |
| 2012/0283855 A1* | 11/2012 | Hoffman ................ G01C 21/20 700/91 |
| 2012/0290109 A1* | 11/2012 | Engelberg ........... G06F 19/3481 700/91 |
| 2013/0013331 A1* | 1/2013 | Horseman ........... G06F 19/3418 705/2 |
| 2013/0027411 A1* | 1/2013 | Hebler ................ G06F 19/3418 345/501 |
| 2013/0329081 A1* | 12/2013 | Aronsson ................. H04N 1/32 348/231.2 |

* cited by examiner

100 ↙

Table 130a

| Activity Level | Icon | Pattern |
|---|---|---|
| Very Low | Sad Face | /TestDevice/Home/SadPattern.txt |
| Low | Disappointed Face | Lights 1 and 11 on; Lights 3-9 on; Fade out lights 3, 4, 5, 7, 8, and 9; Flash lights 1 and 11; Fade out lights 1, 6, and 11 |
| Medium | Happy Face | Lights 1 and 11 on; Lights 3-9 on |
| High | Excited Face | Lights 1 and 11 on; Lights 3-9 fade on |

*Fig. 1C*

Table 130b

| % of Goal achieved | Icon | Pattern |
|---|---|---|
| 0-50% | Disappointed Face | Lights 1 and 11 on; Lights 3-9 on; Fade out lights 3, 4, 5, 7, 8, and 9; Flash lights 1 and 11; Fade out lights 1, 6, and 11 |
| 50-90% | Happy Face | 75-90%: Lights 1, 3-9, and 11 on |
| | | 50-74%: Lights 1 and 11 on; Lights 3-9 fade on clockwise |
| 90-100+% | Excited Face | Lights 1 and 11 on; Lights 3-9 fade on |

*Fig. 1D*

METHODS AND SYSTEMS FOR DISPLAYING REPRESENTATIONS OF FACIAL EXPRESSIONS AND ACTIVITY INDICATORS ON DEVICES

CROSS-REFERENCE TO RELATED APPLICATIONS

This application claims priority from U.S. Provisional Patent Application No. 61/857,016, filed on Jul. 22, 2013, entitled "Methods and Systems for Displaying Representations of Facial Expressions and Activity Indicators on Devices," which is hereby incorporated by reference.

BACKGROUND

The disclosure relates to generating displays on devices. More particularly, the methods and systems described herein relate to displaying representations of facial expressions and activity indicators on personal fitness devices.

In conventional systems, a personal fitness device uses text messages and icons to motivate a user of the personal fitness device. However, in such systems, the icons and messages are typically selected based on a level of activity of the user of the personal fitness device. Such systems do not typically provide functionality for selecting icons or messages to display based on a level of progress towards a user objective. Nor do such systems typically provide an indication of a type of activity the personal fitness device is monitoring.

BRIEF SUMMARY

Users of devices such as personal fitness devices often use these devices while undertaking vigorous physical activities, such as walking, running, swimming, and cycling. In some aspects, methods and systems described herein provide users engaged in such activities with user interfaces that convey data with minimal user input and attention. For example, in one embodiment, a user interface on a personal fitness device provides succinct and useful information accessible to the user while requiring a minimal amount of time to view the user interface; such a user interface may be said to provide a "glance-able" display.

In one aspect, a method for displaying representations of facial expressions on devices includes receiving, by a processor on a device, data from a sensor coupled to the device. The method includes identifying, by the processor, responsive to the received data, a level of progress that a user of the device made towards a goal. The method includes selecting, by the processor, responsive to the identification, an icon representing a facial expression. The method includes modifying, by the processor, a level of power for each of a plurality of light indicators embedded in the device to display the icon.

In another aspect, a method for displaying a representation of a type of activity monitored by a device includes receiving, by a processor on a device, data from a sensor coupled to the device. The method includes identifying, by the processor, responsive to the received data, a type of activity of a user of the device. The method includes selecting, by the processor, responsive to the identification, at least one icon representing the type of activity. The method includes modifying, by the processor, a level of power for each of a plurality of light indicators embedded in the device to display the icon.

In still another aspect, a method for displaying a representation of a type of activity monitored by a device includes receiving, by a processor on a device, from a user of the device, an identification of a type of activity undertaken by the user. The method includes identifying, by the processor, responsive to the received data, a type of activity of a user of the device. The method includes selecting, by the processor, responsive to the identification, at least one icon representing the type of activity. The method includes modifying, by the processor, a level of power for each of a plurality of light indicators embedded in the device to display the icon.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 1C is a block diagram depicting an embodiment of a table accessible by a processor for selecting an icon in a plurality of icons to represent a facial expression on a device;

FIG. 1D is a block diagram depicting another embodiment of a table accessible by a processor for selecting an icon in a plurality of icons to represent a facial expression on a device;

DETAILED DESCRIPTION

Figure 1A:
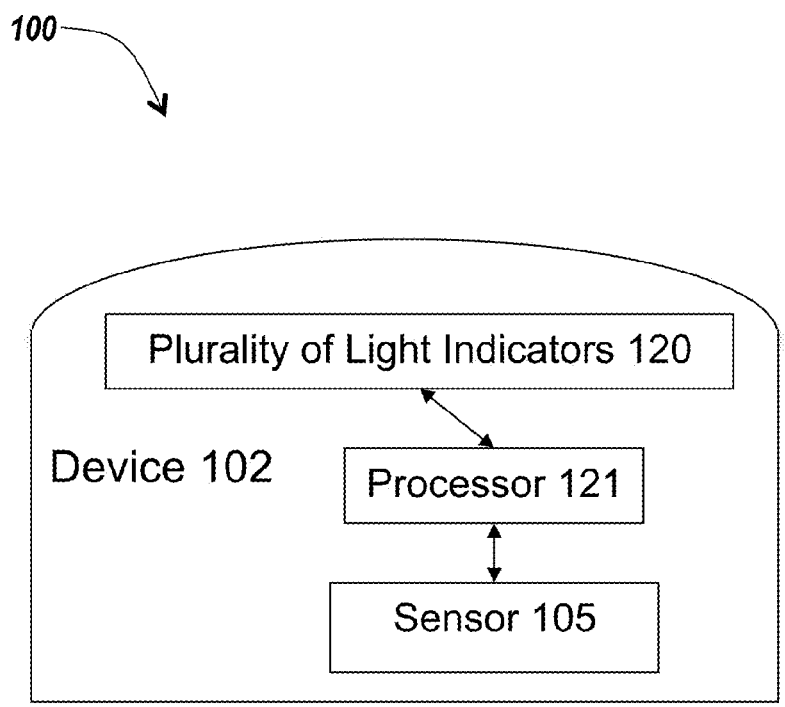
FIG. 1A is a block diagram depicting an embodiment of a system for representing facial expressions on a device.
Figure 1B:
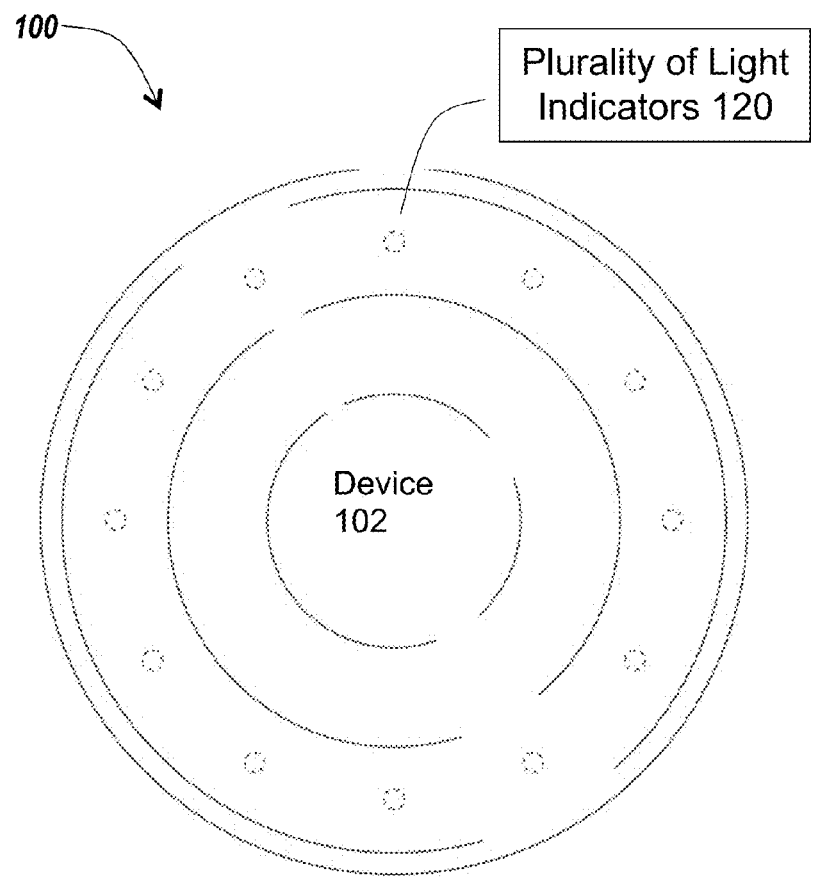
FIG. 1B is a block diagram depicting an embodiment of a device with a plurality of light indicators for representing facial expressions.

Referring now to FIG. 1A, a block diagram depicts an embodiment of a system for representing facial expressions on a device. The system includes a device 102, a sensor 105, a processor 121, and a plurality of light indicators 120.

Referring again to FIG. 1A, the system includes a device 102. In some embodiments, the device 102 is a personal fitness device. Personal fitness devices include, without limitation, stand-alone devices (such as pedometers) and applications integrated into other devices (such as an application executed by a mobile phone, personal digital assistant, or other computing device, the application providing functionality such as tracking distances walked or run by a user). In some embodiments, the personal fitness device includes one or more sensors 105 for monitoring, tracking, and/or otherwise determining data including physical parameters associated with an individual. The device 102 may include at least one data store (not shown) for storing data such as, without limitation, data associated with the individual, the physical parameters/data, and one or more computer program instructions for executing the methods described herein. The device 102 may also include one or more processors 121 for controlling operation of the device 102. The device 102 may also include one or more communication components for wirelessly communicating, to one or more other computing devices, the stored physical parameters and/or physical parameters acquired in real-time and/or during the course of use by the user. The device 102 can also include one or more power sources.

The physical parameters can be physiological, geospatial/timing, and/or the like. Examples of physiological parameters include, but are not limited to, heart and/or pulse rate, blood pressure, muscle electrical potential, nerve electrical potential, temperature, brain waves, motion, measures of activity, number of steps taken, and/or the like. Examples of geospatial and/or timing parameters include but are not limited to, location, acceleration, pace, distance, altitude, direction, velocity, speed, time elapsed, time left, and/or the like. Accordingly, the one or more sensors 105 can include, but are not limited to, one or more temperature sensors, electrical sensors, conductance sensors, accelerometers, magnetometers, capacitive sensors, optical sensors, cameras, global positioning system (GPS) sensors, and/or the like.

The one or more communication components can be implemented in software (e.g., as a communication module stored in the storage media or of the one or more processors 121) and/or hardware (e.g., as a separate circuit, antenna, speakers, light emitting diodes (LEDs), etc.) to enable any suitable communication protocol. The communication protocol can include, but is not limited to, Bluetooth, low power Bluetooth (BLE), near field communication (NFC), radio frequency (RF), Wi-Fi, and/or the like. In some embodiments, the communication protocol can include audio-based protocols such as using a modem to transmit data using audio frequencies and/or ultrasonic frequencies. In some embodiments, the communication protocol can include light-based optical data transfer, such as a pattern of blinking LEDs, for example. In some embodiments, the communication protocol can encompass variations of a magnetic field associated with the device 102, such as with an electromagnet of the device 102.

The one or more data stores (not shown) of the device 102 can be any suitable storage media for storing the physical parameters. In some embodiments, the storage media include non-transitory computer-readable media. In some embodiments, the storage media include non-volatile computer storage media such as flash memory, EEPROM (Electrically Erasable Programmable Memory), FRAM (Ferroelectric Random Access Memory), NVRAM, (Non Volatile Random Access Memory), SRAM (Static Random Access Memory), and DRAM (Dynamic Random Access Memory). The one or more processors 121 can be any suitable processing device for controlling operation of the various components of the device 102. In some embodiments, one or more modules are implemented on the storage media and/or the processor 121 for controlling operation of the device 102.

The one or more power sources of the device 102 can include, but is not limited to, replaceable batteries such as button cells, an integrated battery, a rechargeable battery, capacitors, super-capacitors, and/or the like.

In one embodiment, a user operates the device 102 to collect user-specific information, such as physical parameters associated directly or indirectly with the user. In some embodiments, the device 102 can include a personal fitness device or activity tracker such as, but not limited to, a pedometer, a physiological monitor such as a heart rate monitor, a respiration monitor, a GPS system (including GPS watches), and/or the like.

Figure 2A:
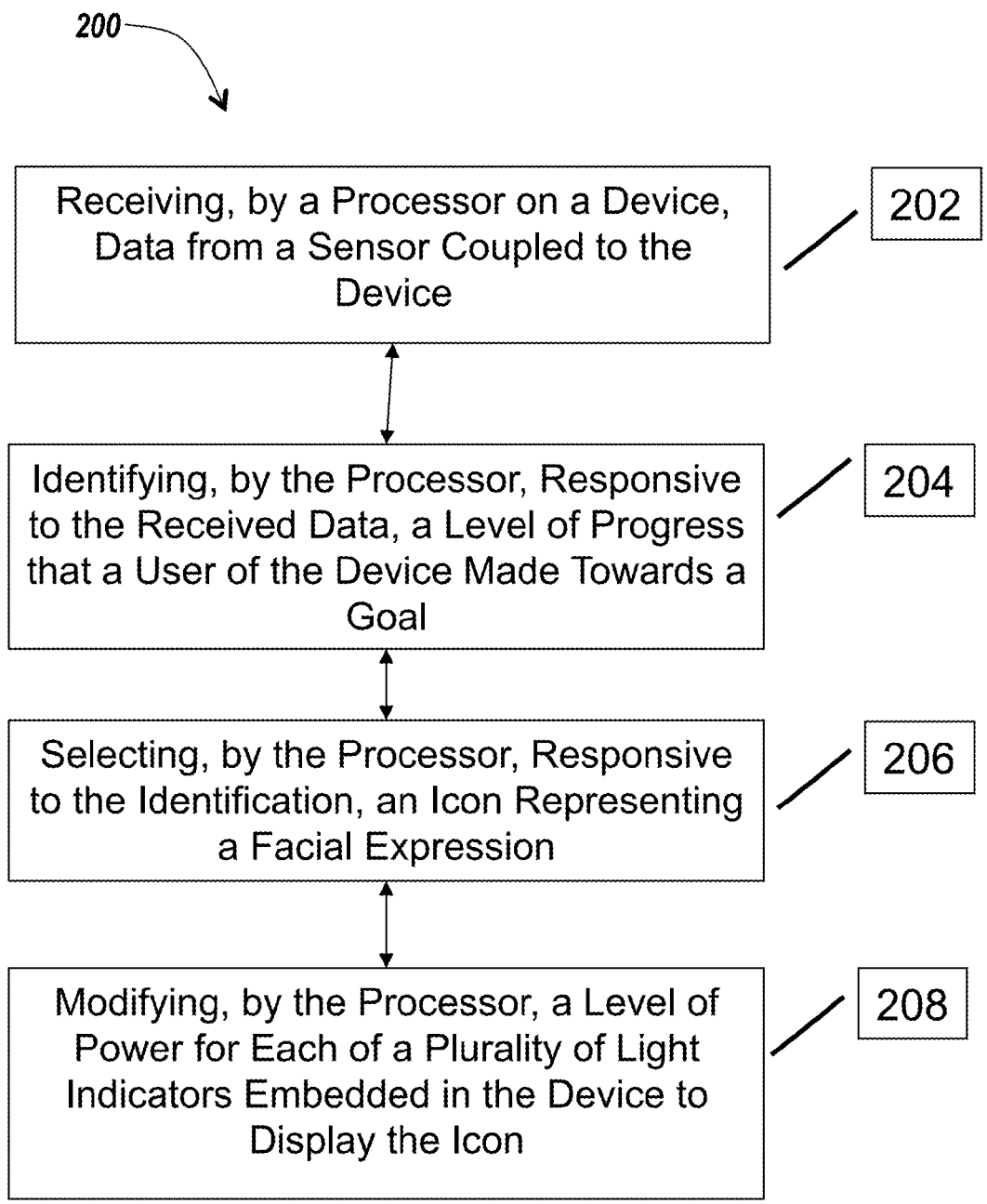
FIG. 2A is a flow diagram depicting an embodiment of a method for representing facial expressions on a device.

Referring now to FIG. 2A, a flow diagram depicts an embodiment of a method for representing facial expressions on a device. In brief overview, the method 200 includes receiving, by a processor on a device, data from a sensor coupled to the device (202). The method 200 includes identifying, by the processor, responsive to the received data, a level of progress that a user of the device made towards a goal (204). The method 200 includes selecting, by the processor, responsive to the identification, an icon representing a facial expression (206). The method 200 includes modifying, by the processor, a level of power for each of a plurality of light indicators embedded in the device to display the icon (208).

Referring now to FIG. 2A in greater detail, the method 200 includes receiving, by a processor on a device, data from a sensor coupled to the device (202). As described above, the sensor 105 may monitor one or more physical parameters and generate data associated with the monitored one or more physical parameters. The sensor 105 may transmit the generated data to the processor 121. Alternatively, the sensor 105 may store the generated data in a data store accessible by the processor 121.

The processor identifies, responsive to the received data, a level of progress that a user of the device made towards a goal (204). In one embodiment, a user has specified a goal such as, without limitation, a number of steps to take, an amount of time to be physically active, a level of physical activity to achieve during a particular period, or a type of activity to undertake. In some embodiments, the user accesses a second device 102b (not shown) to specify the goal. For example, the user may access a software application executed by a second device 102b or a computing device 102*b* (e.g., a laptop, personal digital assistant, smartphone, or other computer) and the software application may transmit goal-related data to the processor 121 during a syncing operation. In other embodiments, the user provides goal-related data directly to the processor 121.

In one embodiment, the processor 121 determines, based upon the data received from the sensor 105, that the user is making progress towards completing a goal. In another embodiment, the processor 121 determines, based upon the data received from the sensor 105, that the user is not making progress towards completing a goal. The processor 121 may determine a level of progress that the user has made based on the received data. For example, the processor 121 may determine from the received data an amount of activity (e.g., a number of steps walked, a number of laps around a pool, and a number of miles bicycled or run), compare the amount of the activity with a desired amount of activity specified in the goal, and calculate a percentage of the desired amount of activity achieved. As another example, in some embodiments, the sensor 105 includes an accelerometer and measures a level of activity by analyzing an accelerometer signal and quantifying the level of activity via an algorithm such as, by way of example, an algorithm for quantifying distances (e.g., steps and miles). In one of these embodiments, the processor 121 compares the quantified level of activity to a threshold set by the user in a user application to determine a percentage of a user goal completed by the user. In another of these embodiments, the threshold is pre-determined by the application. In still another of these embodiments, the processor 121 compares the quantified level of activity to one of a plurality of thresholds (e.g., one threshold for each of a plurality of activity types or one threshold for each of a plurality of levels of activity). In yet another of these embodiments, the processor 121 compiles the results from comparing the quantified level of activity to a plurality of thresholds to determine a level of progress.

The processor selects, responsive to the identification, an icon representing a facial expression (206). The processor 121 may access a table to select one of a plurality of icons. The icons may include, without limitation, a happy face, a sad face, a winking face, a disappointed face, and an excited face. In one embodiment, icons include expressions selected to provide feedback (positive or negative) to a user regarding his or her current level of activity. In another embodiment, icons include expressions selected to motivate a user of the device 102 to modify his or her current level of activity.

Referring now to FIG. 1C, a block diagram depicts one embodiment of a table 130*a* accessible by the processor 121 for selecting an icon in a plurality of icons to represent a facial expression to a user of a device 102. The table 130*a* may include an instruction to the processor 121 as to how to represent the icon on the device. In the example shown in FIG. 1C, the table 130*a* identifies each light indicator in the plurality of light indicators 120 by an identifier, such as a number (e.g., 1, 2, 3, . . . n). It should be understood that numbering each of the plurality of light indicators 120 is only one example of how the table 130*a* may identify each of the plurality of light indicators 120; in other embodiments, the table 130*a* identifies each of the plurality of light indicators 120 using other identifiers. In other embodiments, the table 130*a* may include an identification of a location in a data store from which the processor 121 may retrieve instructions. In the example shown in FIG. 1C, the table 130*a* indicates that if the processor 121 determines, based on data received from sensor 105, that the user has a very low activity level, the processor 121 should display a "sad face" icon. The table 130*a* further indicates that, for the purposes of this example, the processor 121 should retrieve instructions for how to display the "sad face" icon from a "SadPattern.txt" file in a "home" sub-directory of a "TestDevice" directory. The table 130*a* may include specific metrics with which the processor 121 may quantify sensor data into various levels of activity. Alternatively, the table 130*a* may refer the processor 121 to a second table (not shown) with which the processor 121 may quantify the received sensor data. As another example, the table 130*a* indicates that if the processor 121 determines, based on data received from sensor 105, that the user has a low activity level, the processor 121 should display a "disappointed face" icon. In this example, the table 130*a* specifies the order in which the processor 121 should power on and off a plurality of light indicators 120. In another embodiment, the processor 121 accesses a look-up table to retrieve patterns stored in memory on the device 102. In still another embodiment, the processor 121 accesses data memory into which a structure or array has been hardcoded indicating which light indicators 120 to turn on and when to turn them on. In another embodiment, the processor 121 accesses data memory into which an algorithm has been hardcoded, the processor 121 executing the algorithm periodically to determine which light indicators 120 to turn on at each step of an animation. In yet another embodiment, some patterns (e.g., progress animations) are represented as a combination of these embodiments depending on the value of the input progress percentage (e.g., certain percentage values use an algorithm while others access data structures hardcoded into memory). In other embodiments, depending on a data range provided as a level of progress, the processor 121 will follow a particular pattern to play a specific animation.

Referring now to FIG. 1D, a block diagram depicts one embodiment of a table 130*b* accessible by the processor 121 for selecting an icon in a plurality of icons to represent a facial expression to a user of a device 102. In this embodiment, the table 130*b* specifies which icons the processor 121 should display based on a percentage of a goal accomplished by a user of the device 102.

The processor modifies a level of power for each of a plurality of light indicators embedded in the device to display the icon (208). In one embodiment, the processor 121 modifies the level of power of one of the plurality of light indicators 120 by turning the light indicator on. In another embodiment, the processor 121 modifies the level of power of one of the plurality of light indicators 120 by turning the light indicator off. In one embodiment, the processor 121 modifies the level of power of one of the plurality of light indicators 120 by gradually lowering the power of the light indicator until the processor 121 turns off the light indicator. In another embodiment, the processor 121 modifies the level of power of one of the plurality of light indicators 120 by quickly and/or abruptly lowering the power of the light indicator until the processor 121 turns off the light indicator. In still another embodiment, the processor 121 modifies the level of power of one of the plurality of light indicators 120 by gradually increasing the power of the light indicator until the processor 121 turns on the light indicator. In another embodiment, the processor 121 modifies the level of power of one of the plurality of light indicators 120 by quickly and/or abruptly increasing the power of the light indicator until the processor 121 turns on the light indicator. In still another embodiment, the processor 121 executes a sequence of power modification instructions to create a pattern of lights on the device that represent a facial expression. In yet another embodiment, the processor 121 modifies the level of power by transmitting an instruction to a power control component (e.g., an LED driver chip, an individual transistor, or another microcontroller) that controls a level of power available to each light indicator. In some embodiments in which the plurality of light indicators 120 are provided as light emitting diodes (LEDs), the processor 121 controls the brightness of the LEDs by quickly flashing the LEDs on and off and controlling the on-time of each flash using pulse width modulation. In other embodiments in which the plurality of light indicators 120 are provided as LEDs, the processor 121 controls the brightness of the LEDs by controlling the drive current of the microcontroller output pin and/or changing the resistance in series with the LED.

Figure 1E:
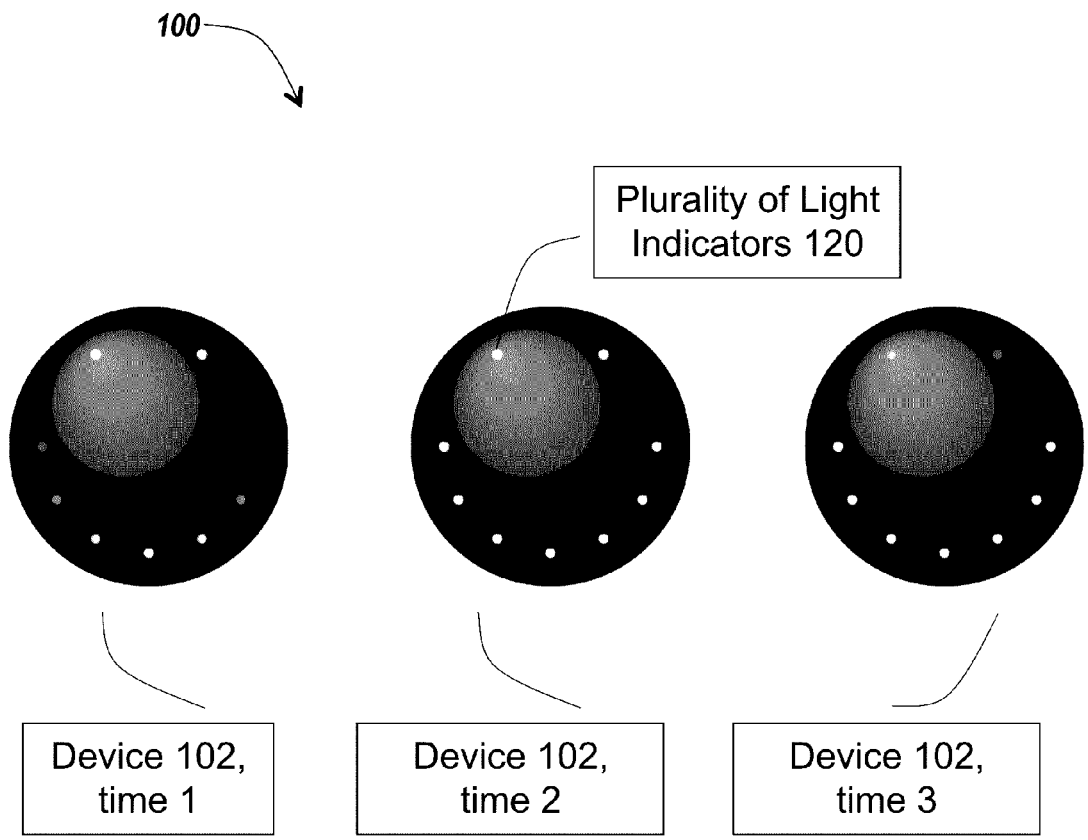
FIG. 1E is a block diagram depicting an embodiment of a pattern of modifications to a level of power of one or more of a plurality of light indicators to display a representation of a facial expression.

FIG. 1E is a block diagram depicting one embodiment of a pattern of modifications to a level of power of one or more of a plurality of light indicators 120 to display a representation of a facial expression. As depicted in FIG. 1E, the processor 121 may modify a level of power of one or more of the plurality of light indicators 120 in a particular sequence over time. For example, and as shown in FIG. 1E, at a first point in time the processor 121 may first turn on two lights that represent eyes and then slowly turn on a subset of the plurality of light indicators 120 so that at a second point in time, the device displays a facial expression (a smiling face in FIG. 1E). After displaying the facial expression, the processor 121 may, at a third point in time, begin to turn of the lights by first turning off the lights that represented eyes and then fading out the lights that represented the smile.

Figure 1F:
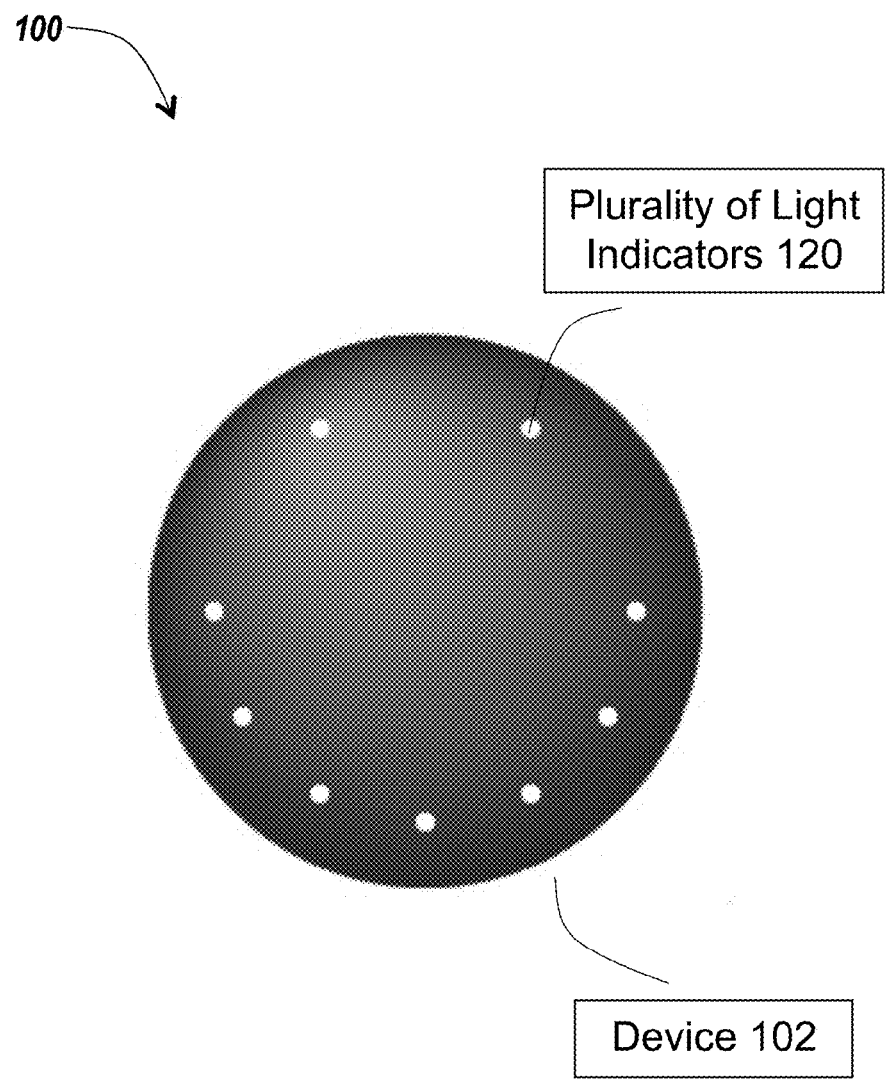
FIG. 1F is a block diagram depicting another embodiment of a pattern of modifications to a level of power of one or more of a plurality of light indicators to display a representation of a facial expression.

FIG. 1F is a block diagram depicting another embodiment of a pattern of modifications to a level of power of one or more of a plurality of light indicators 120 to display a representation of a facial expression. As depicted in FIG. 1F, the processor 121 may modify a level of power of one or more of the plurality of light indicators 120 in a particular sequence over time. Although in some embodiments, the processor 121 gradually modifies the level of power over time and may modify a level of power for a first in the plurality of light indicators 120 at a different time than it modifies the level of power for a second in the plurality of light indicators 120, in other embodiments, and as shown in FIG. 1F, the processor 121 makes the modification at substantially the same time. Referring back to FIG. 1D, the processor 121 may access a table 130 to determine whether to turn one or more light indicators in the plurality of light indicators 121 on at substantially the same time or over a period of time. As shown in FIG. 1D, the table 130b may indicate that if a user has achieved first level of progress, the processor 121 should modify the power to at least one the light indicators 120 gradually and if the user has achieved a second level of progress, the processor 121 should modify the power to at least one of the light indicators 120 at substantially the same time (for example, and without limitation, if the user has achieved between 50% and 74% of a goal, the processor 121 should turn lights 1 and 11 on at substantially the same time and gradually fade on lights 3-9, but if the user has achieved between 75 and 90% of the goal, the processor 121 should turn lights 1, 3-9, and 11 on at substantially the same time). In other embodiments, a user may specify whether the user prefers lights to be turned on at substantially the same time or gradually over a particular period of time (e.g., by accessing an application in which the user can customize preferences or settings for the device 102).

Figure 1G:
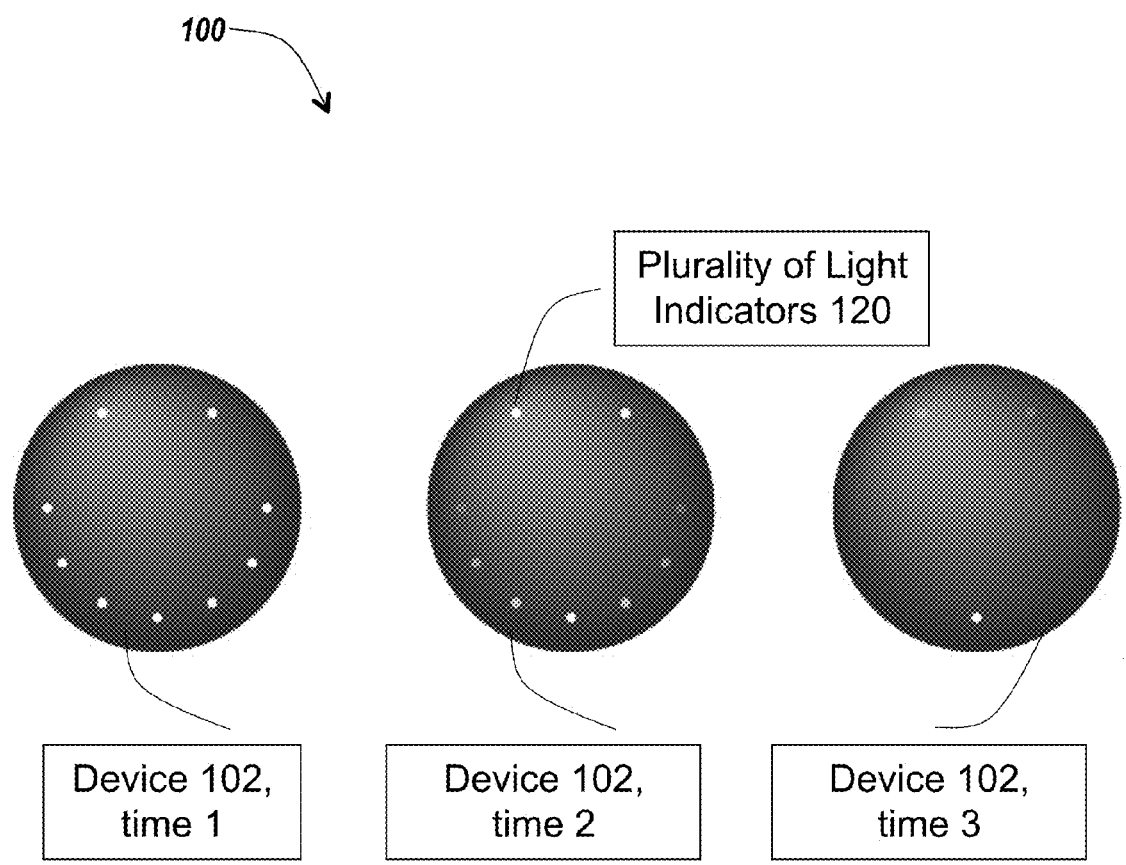
FIG. 1G is a block diagram depicting one embodiment of a pattern of modifications to a level of power of one or more of a plurality of light indicators to display a representation of a facial expression conveying disappointment.

Referring now to FIG. 1G, a block diagram depicts one embodiment of a pattern of modifications to a level of power of one or more of a plurality of light indicators 120 to display a representation of a facial expression conveying disappointment. As depicted in FIG. 1G, the processor 121 may modify a level of power of one or more of the plurality of light indicators 120 in a particular sequence over time. In FIG. 1G, the pattern of modifications results in a display of a disappointed face.

Figure 1H:
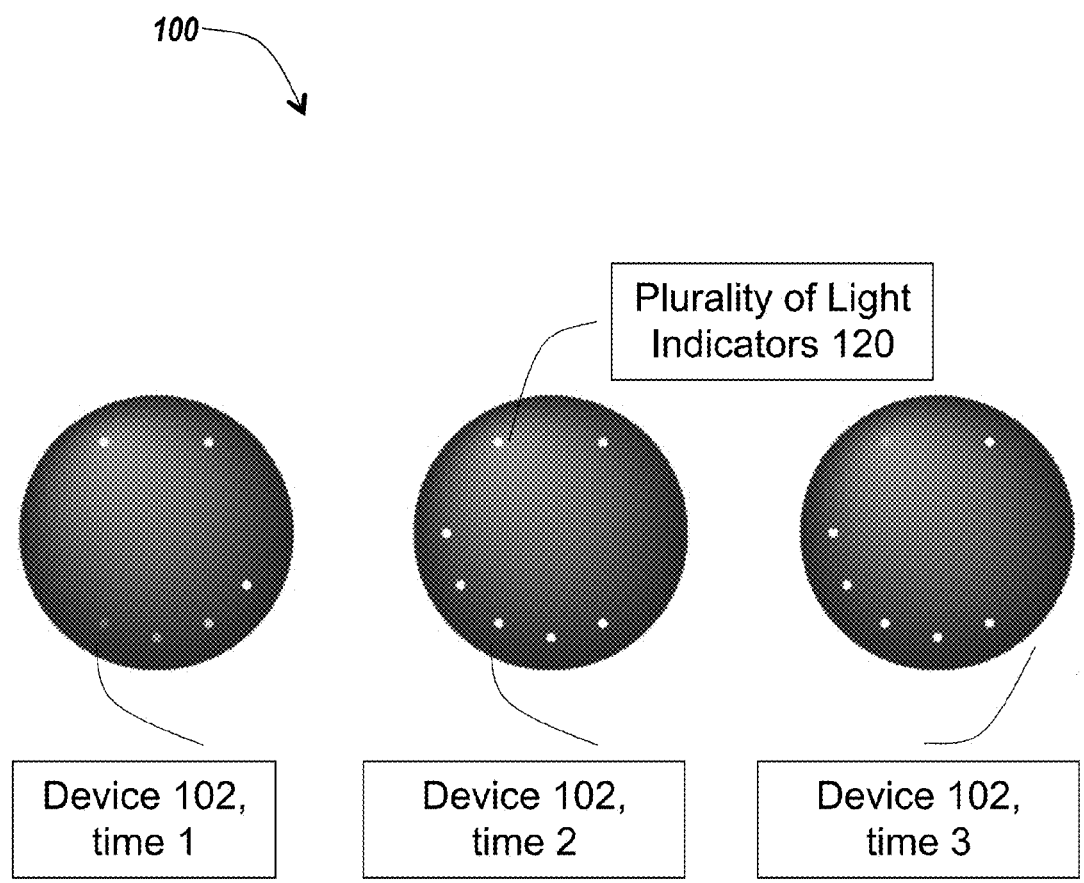
FIG. 1H is a block diagram depicting one embodiment of a pattern of modifications to a level of power of one or more of a plurality of light indicators to display a representation of a facial expression conveying a winking face.

Referring now to FIG. 1H, a block diagram depicts one embodiment of a pattern of modifications to a level of power of one or more of a plurality of light indicators 120 to display a representation of a facial expression conveying a winking face. As depicted in FIG. 1H, the processor 121 may modify a level of power of one or more of the plurality of light indicators 120 in a particular sequence over time. In FIG. 1H, the pattern of modifications results in a display of a winking face.

Figure 1I:
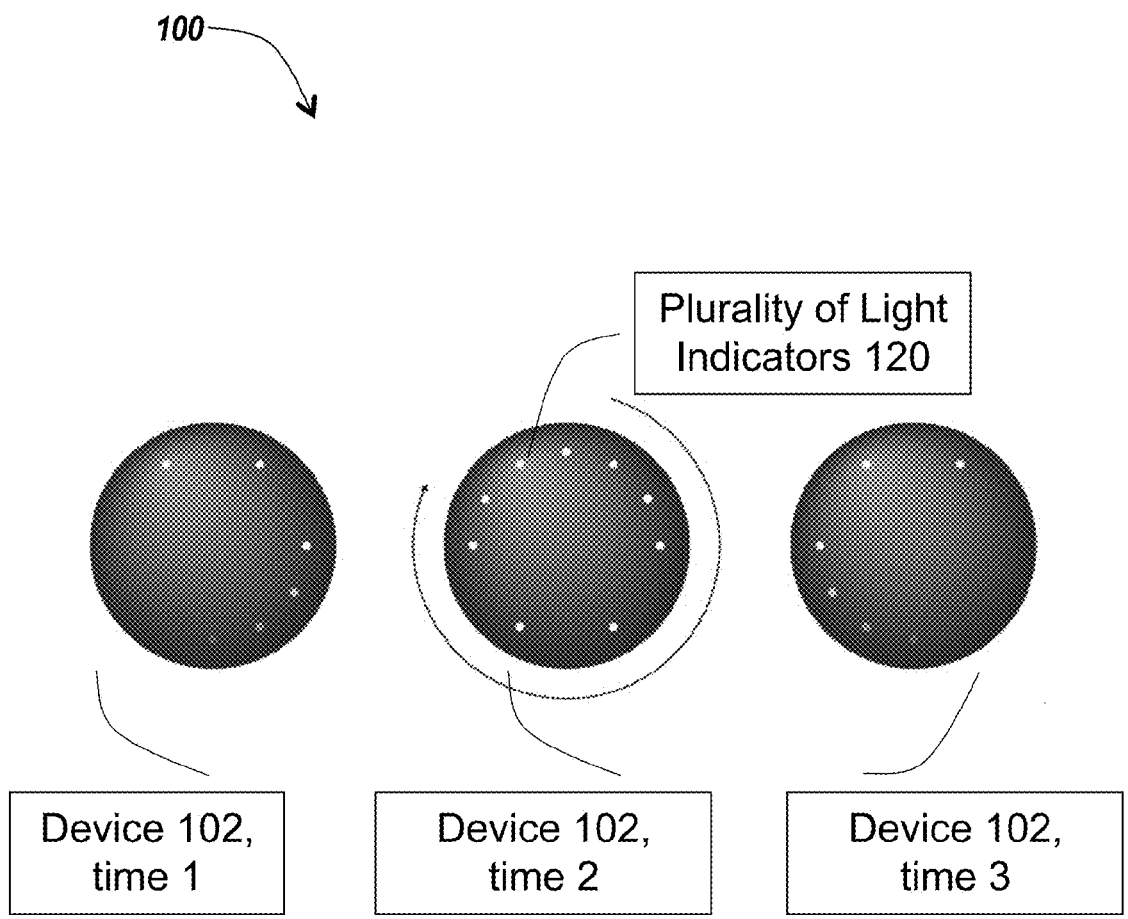
FIG. 1I is a block diagram depicting one embodiment of a pattern of modifications to a level of power of one or more of a plurality of light indicators to display a representation of a facial expression conveying excitement.

Referring now to FIG. 1I, a block diagram depicts one embodiment of a pattern of modifications to a level of power of one or more of a plurality of light indicators 120 to display a representation of a facial expression conveying excitement. As depicted in FIG. 1I, the processor 121 may modify a level of power of one or more of the plurality of light indicators 120 in a particular sequence over time. In FIG. 1I, the pattern of modifications results in a display of an excited face.

In some embodiments, the processor 121 selects the icon and modifies the level of power to the plurality of light indicators 120 at a pre-determined time. In other embodiments, the processor 121 selects the icon and modifies the level of power to the plurality of light indicators 120 upon determining that a user has achieved a predetermined portion of a goal. In still other embodiments, the processor 121 selects the icon and modifies the level of power to the plurality of light indicators 120 upon receiving an instruction from a user. In one of these embodiments, the user physically interacts with the device 102 to provide the instruction. For example, the user may tap the device 102 a pre-determined number of times to instruct the processor 121 to display the facial expression. As another example, the user may hold the device 102 in a particular way for a pre-determined period of time to trigger the display of the facial expression; for example, and without limitation, the user may move the device 102 into a pre-determined position such as moving the device towards the user's face and holding the device at a particular angle for a particular period of time as if, for example, the user were looking at a wristwatch.

Figure 2B:
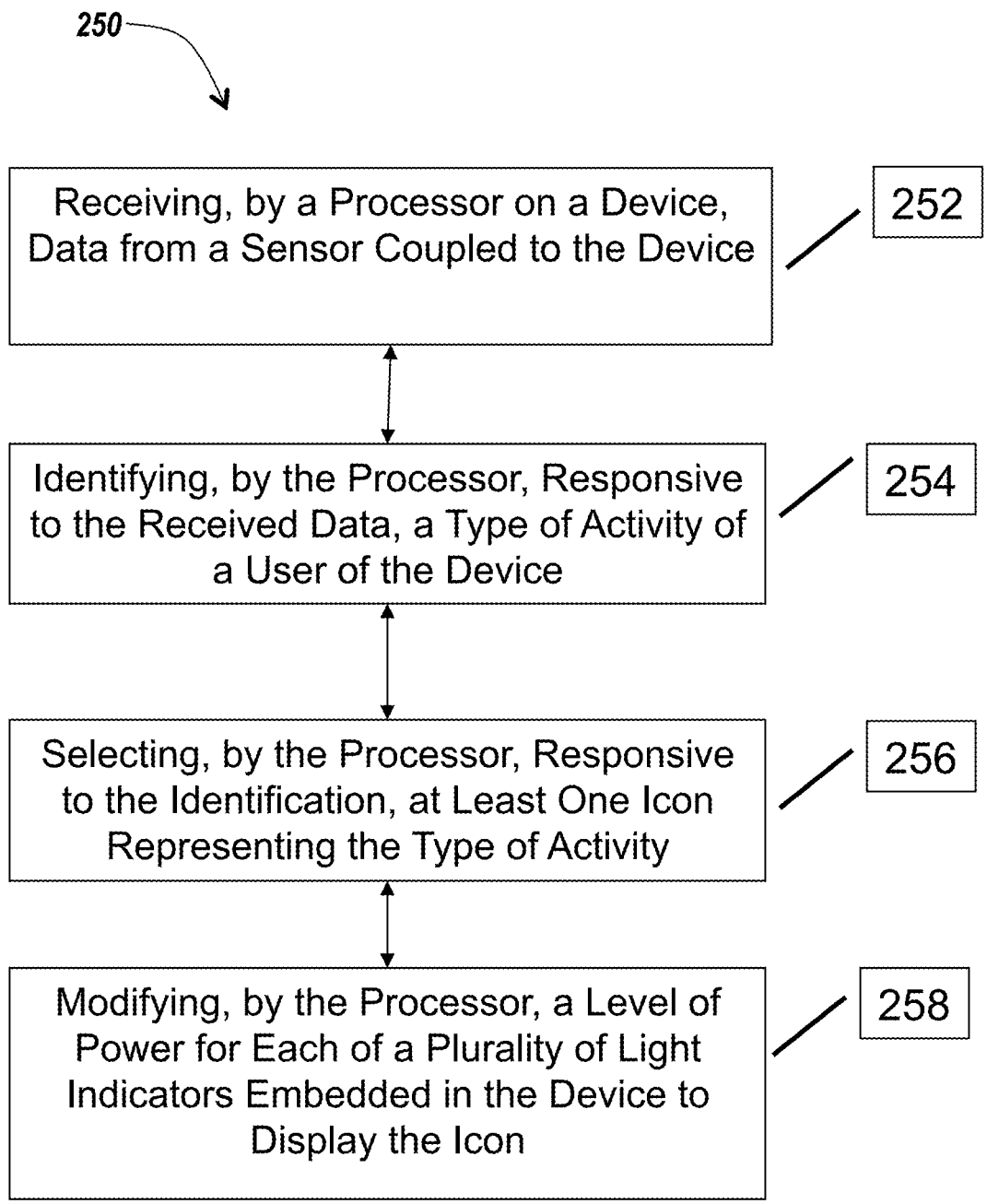
FIG. 2B is a flow diagram depicting an embodiment of a method for representing a type of activity monitored by a device.

Referring now to FIG. 2B, a flow diagram depicts an embodiment of a method for representing a type of activity monitored by a device. In brief overview, a method 250 includes receiving, by a processor on a device, data from a sensor coupled to the device (252). The method 250 includes identifying, by the processor, responsive to the received data, a type of activity of a user of the device (254). The method 250 includes selecting, by the processor, responsive to the identification, at least one icon representing the type of activity (256). The method 250 includes modifying, by the processor, a level of power for each of a plurality of light indicators embedded in the device to display the icon (258).

Referring now to FIG. 2B in greater detail, the method 250 includes receiving, by a processor on a device, data from a sensor coupled to the device (252). In one embodiment, the processor 121 receives the data as described above in connection with FIG. 2A.

The processor identifies, responsive to the received data, a type of activity of a user of the device (254). Types of activities may include, without limitation, walking, running, cycling, and swimming. In one embodiment, the processor 121 uses a received level of acceleration to determine the type of activity. For example, a high level of acceleration may indicate that the user of the device is running or bicycling instead of walking. In another embodiment, the processor 121 uses a received motion signature to determine the type of activity. For example, if the sensor 105 determines that the user is moving in a cyclical pattern at a first speed, the sensor 105 provides a first motion signature with which the processor 121 may determine that the device 102 is coupled to the user's leg or foot and that the user is bicycling; alternatively, if the sensor 105 determines that the user is moving in a cyclical pattern at a second speed, the sensor 105 provides a second motion signature with which the processor 121 may determine that the device 102 is coupled to the user's wrist and that the user is swimming. In other embodiments, the user can manually specify a type of activity (e.g., by identifying, in a software application, a type of activity undertaken at or scheduled for a particular time and having the software application transmit the identification to the device 102, e.g., during a synchronization operation) and the processor 121 receives the specified type. In further embodiments, the user can specify a type of activity by physically interacting with the device 102 in a predetermined manner. For example, the user may tap the device 102 (or triple tap, or execute any other predetermined interaction) to indicate that the user is about to start a specific activity. In such an example, the user may have provided the device 102 with an indication of what activity to associate with the physical interaction, for example, by specifying a preference in a software application that communicates the preference to the processor 121. In another example, the user may execute a physical interaction with the device 102 to cycle through a plurality of activity types (e.g., by tapping the device to cycle through the plurality of activity types). In such an example, the processor 121 may display a representation of each of the plurality of activity types as the user cycles through the plurality.

The processor selects, responsive to the identification, at least one icon representing the type of activity (256). In some embodiments, the processor 121 accesses a table to select an icon, as discussed above in connection with the description of selecting facial expression icons in FIGS. 2A and 1C-1D.

The processor modifies a level of power for each of a plurality of light indicators embedded in the device to display the icon (258). In some embodiments, the processor 121 modifies the level of power, as discussed, above in connection with FIGS. 2A, and 1C-1F.

Figure 1J:
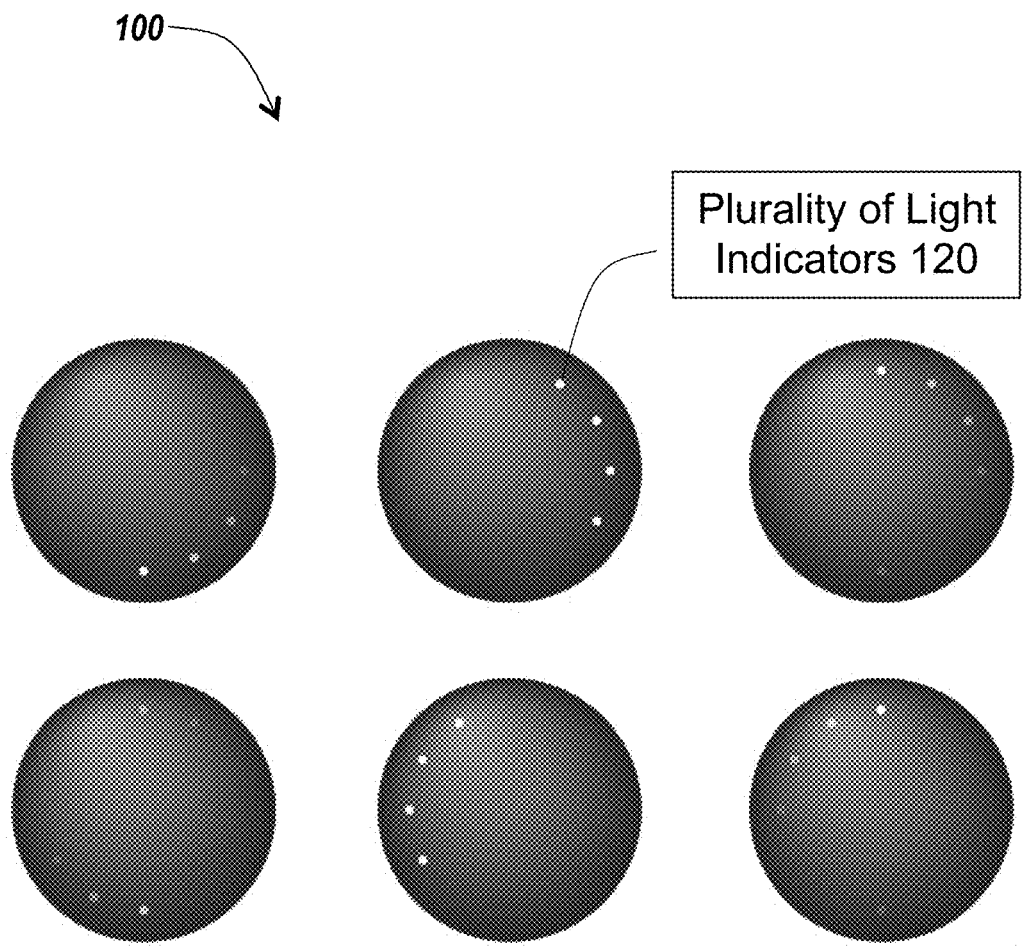
FIG. 1J is a block diagram depicting one embodiment of a pattern of modifications to a level of power of one or more of a plurality of light indicators to display a representation of a type of bipedal activity.

Referring now to FIG. 1J, a block diagram depicts one embodiment of a pattern of modifications to a level of power of one or more of a plurality of light indicators 120 to display a representation of a type of bipedal activity. As depicted in FIG. 1J, the processor 121 may modify a level of power of one or more of the plurality of light indicators 120 in a particular sequence over time. In FIG. 1J, the pattern of modifications result in a display of a plurality of light indicators 120 that are animated in two halves using a plurality of brightness levels fading in from the bottom to the top, mimicking a walking or running beat to represent a stepping motion.

Figure 1K:
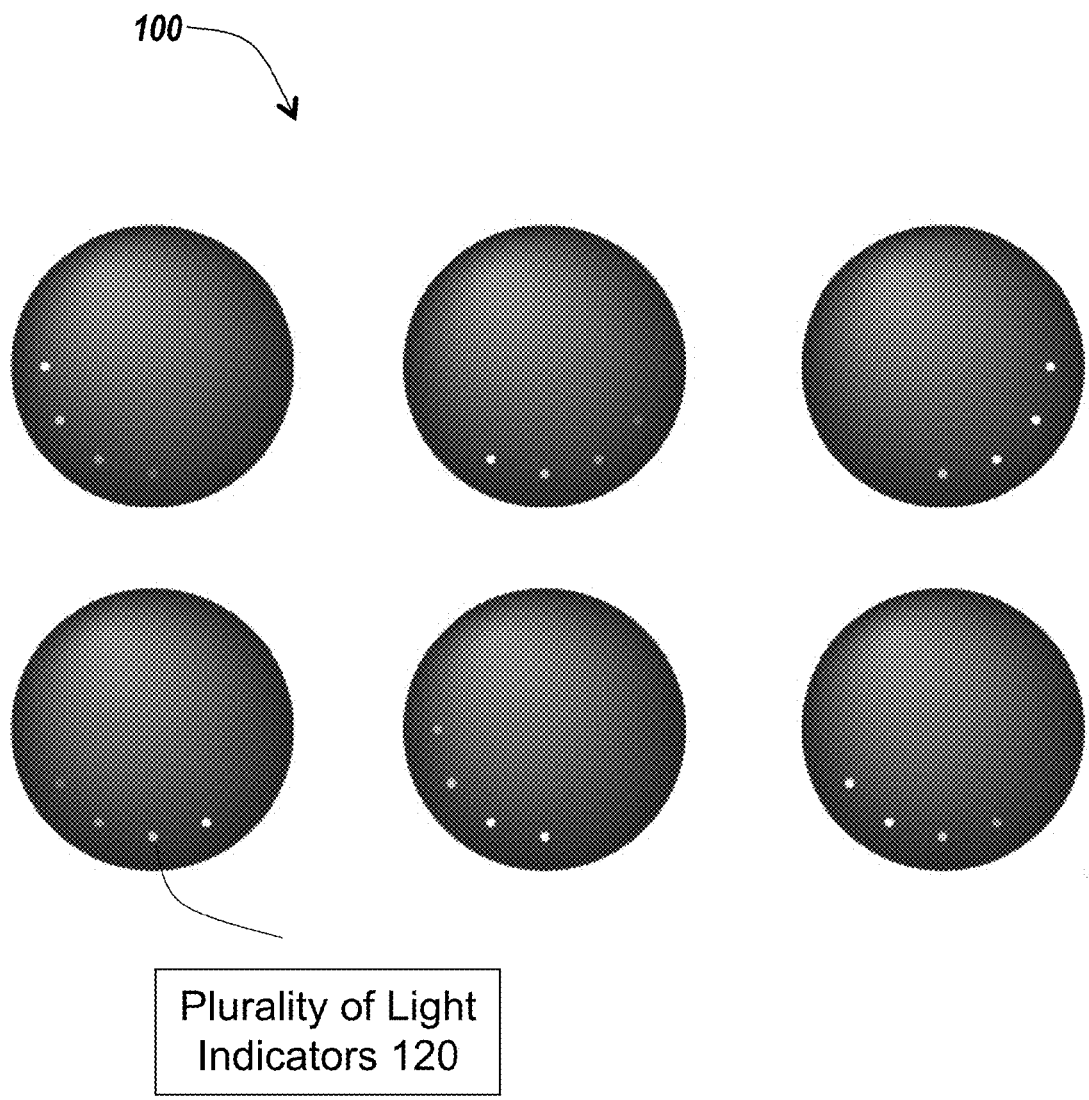
FIG. 1K is a block diagram depicting one embodiment of a pattern of modifications to a level of power of one or more of a plurality of light indicators to display a representation of a type of water-based activity.

Referring now to FIG. 1K, a block diagram depicts one embodiment of a pattern of modifications to a level of power of one or more of a plurality of light indicators 120 to display a representation of a type of water-based activity. As depicted in FIG. 1K, the processor 121 may modify a level of power of one or more of the plurality of light indicators 120 in a particular sequence over time. In FIG. 1K, the pattern of modifications result in a display of a representation of a water-based activity (such as swimming) by having the lights appear to move from side to side in a rocking motion that mimics the movement of water or waves.

Figure 1L:
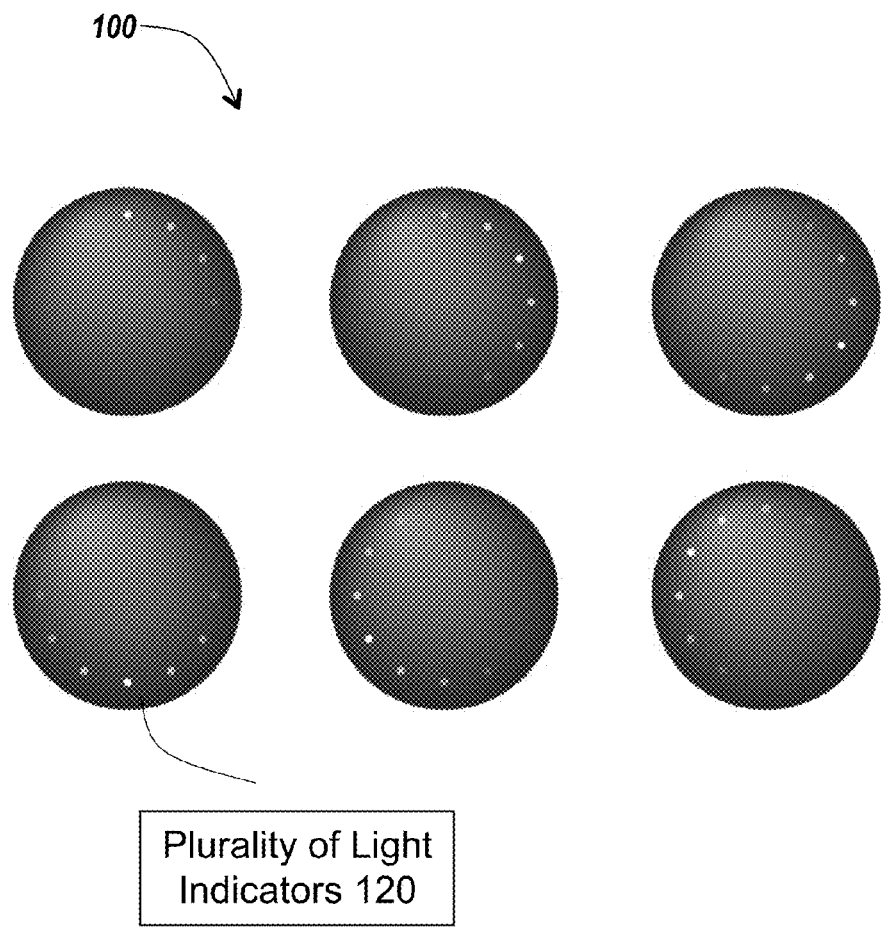
FIG. 1L is a block diagram depicting one embodiment of a pattern of modifications to a level of power of one or more of a plurality of light indicators to display a representation of a type of cycling activity.

Referring now to FIG. 1L, a block diagram depicts one embodiment of a pattern of modifications to a level of power of one or more of a plurality of light indicators 120 to display a representation of a type of cycling activity. As depicted in FIG. 1L, the processor 121 may modify a level of power of one or more of the plurality of light indicators 120 in a particular sequence over time. In FIG. 1L, the pattern of modifications result in a display of a representation of a cycling activity by having the lights appear to rotate in a clockwise motion to mimic the movement of wheels on a bicycle.

It should be understood that the representations described in FIGS. 1E-1L are shown merely for purposes of example and do not constitute a limitation of the methods and systems described herein. Embodiments of the methods and systems described herein may provide representations of any type of facial expression or type of activity.

In some embodiments, implementations of the methods and systems described herein provide interfaces that convey information such as a type of activity undertaken by a user of a device 102. In embodiments in which a type of activity may impact calculations such as calories burned, miles traveled, steps walked and other physical calculations, the processor 121 may be able to increase a level of accuracy in its calculations by correctly identifying a type of activity. In one of these embodiments, by providing the user of the device 102 with an indication as to the type of activity the processor 121 has concluded the user is undertaking, the device 102 confirms for the user that the processor 121 has identified the correct type of activity, thus increasing user confidence in the device 102.

Figure 2C:
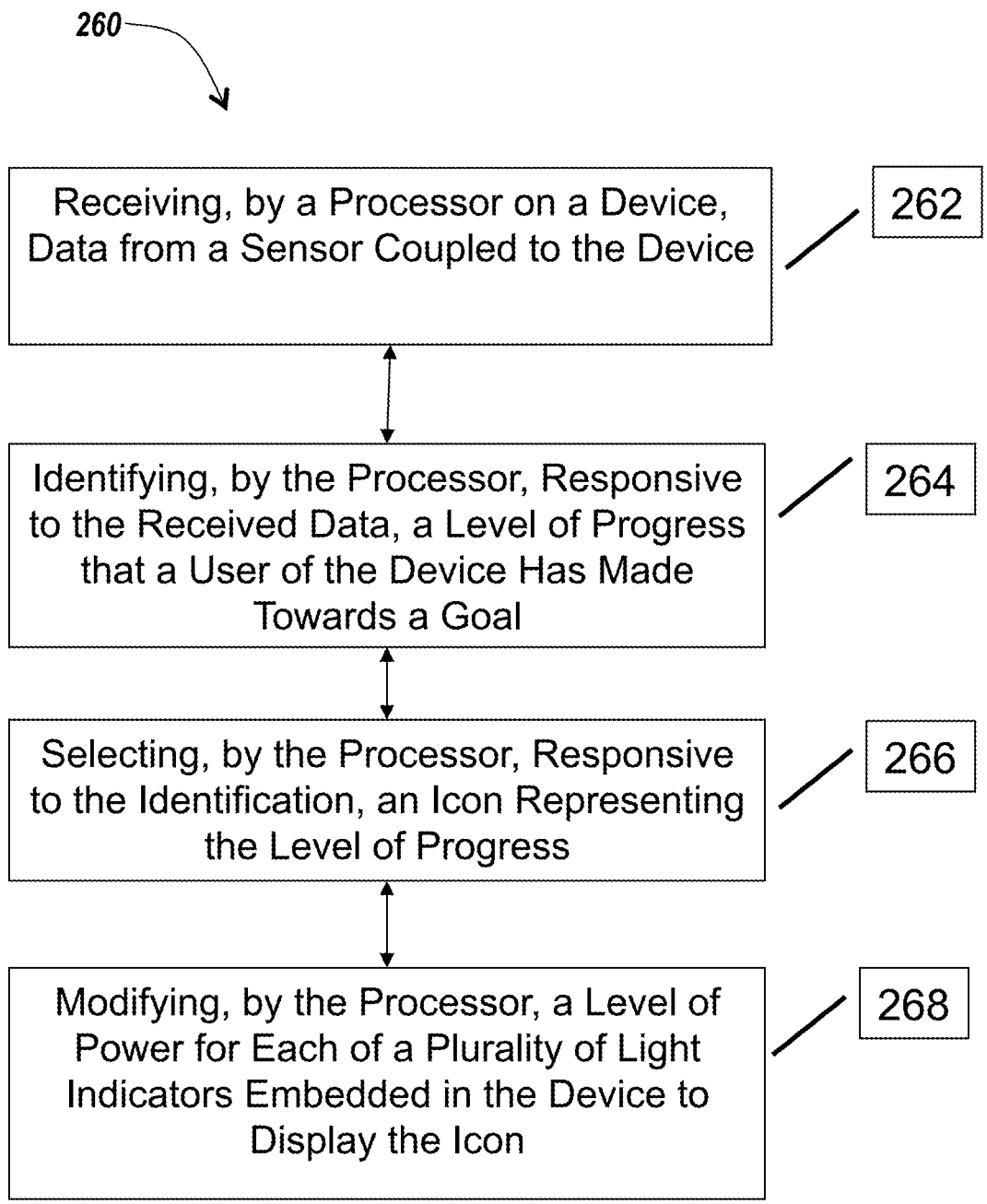
FIG. 2C is a flow diagram depicting an embodiment of a method for representing, on a device, a level of progress a user made towards a goal.

Referring now to FIG. 2C, a flow diagram depicts an embodiment of a method for representing, on a device, a level of progress a user has made towards a goal. In brief overview, the method 200 includes receiving, by a processor on a device, data from a sensor coupled to the device (262). The method 200 includes identifying, by the processor, responsive to the received data, a level of progress that a user of the device has made towards a goal (264). The method 200 includes selecting, by the processor, responsive to the identification, an icon representing the level of progress (266). The method 200 includes modifying, by the processor, a level of power for each of a plurality of light indicators embedded in the device to display the icon (268).

Referring now to FIG. 2C in greater detail, the method 260 includes receiving, by a processor on a device, data from a sensor coupled to the device (262). In one embodiment, the processor 121 receives the data as described above in connection with FIG. 2A.

The processor identifies, responsive to the received data, a level of progress that a user of the device made towards a goal (264). In one embodiment, the processor 121 identifies the level of progress as described above in connection with FIG. 2A.

The processor selects, responsive to the identification, an icon representing the level of progress (266). In some embodiments, the processor 121 accesses a table to select an icon, as discussed above in connection with the description of selecting facial expression icons in FIGS. 2A and 1C-1D. By way of example, and without limitation, the icon may include a progress bar. In such an example, the processor 121 may modify the level of power to at least one of the plurality of light indicators 120 such that the number of lights turned on represents how much progress the user has made.

The processor modifies a level of power for each of a plurality of light indicators embedded in the device to display the icon (268). In some embodiments, the processor 121 modifies the level of power as discussed, as discussed above in connection with FIGS. 2A, and 1C-1F.

Figure 1M:
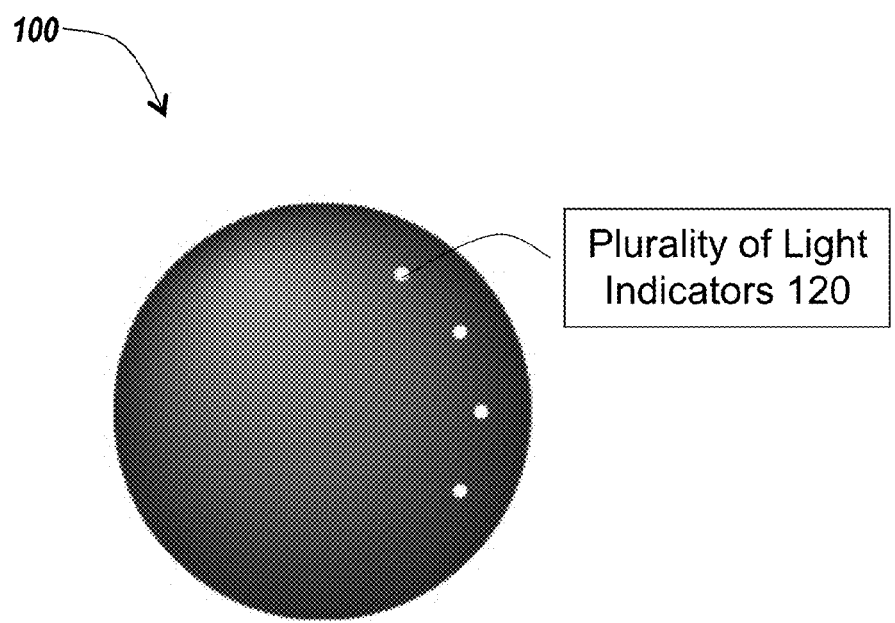
FIG. 1M is a block diagram depicting one embodiment of a pattern of modifications to a level of power of one or more of a plurality of light indicators to display an icon representing a level of progress towards a goal.

Referring now to FIG. 1M, a block diagram depicts one embodiment of an icon representing a level of progress. In the embodiment depicted in FIG. 1M, the icon is a progress bar indicating that the user has achieved less than 50% of a goal. As shown in FIG. 1M, in an embodiment in which the processor 121 determines that the user has achieved 40% of a goal, the processor 121 may determine a total number of lights in the plurality of light indicators 120 and turn on a subset of those lights representing 40%. As another example, if the processor 121 determines that the user has achieved 25% of a goal, the processor 121 would turn on a quarter of the lights and turn on 50% of the lights when the user has achieved 50% of the goal (three lights and six lights, respectively, in an embodiment in which the plurality of light indicators 120 includes 12 lights, for example).

In some embodiments, implementations of the methods and systems described herein provide interfaces that convey information (such as quantities of activity, types of activity, and motivational messaging) using a plurality of light indicators 120 arranged on the surface of a device 102. In one of these embodiments, the use of motion, achieved by fading (or quickly switching) the plurality of light indicators 120 on and off, provides additional information to users of the device 102.

It should be understood that the systems described above may provide multiple ones of any or each of those components and these components may be provided on either a standalone machine or, in some embodiments, on multiple machines in a distributed system.

The systems and methods described above may be implemented as a method, apparatus, or article of manufacture using programming and/or engineering techniques to produce software, firmware, hardware, or any combination thereof. The techniques described above may be implemented in one or more computer programs executing on a programmable computer including a processor, and a storage medium readable by the processor (including, for example, volatile and non-volatile memory and/or storage elements).

Each computer program within the scope of the disclosure may be implemented in any programming language, such as assembly language, machine language, a high-level procedural programming language, or an object-oriented programming language. The programming language may, for example, be LISP, PROLOG, PERL, C, C++, C#, Objective C, JAVA, or any compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of computer-readable devices, firmware, programmable logic, hardware (e.g., integrated circuit chip, electronic devices, a computer-readable non-volatile storage unit, non-volatile memory, such as semiconductor memory devices, including EPROM, EEPROM, and flash memory devices; magnetic disks such as internal hard disks and removable disks; magneto-optical disks; and CD-ROMs). Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium. A computer may also receive programs and data from a second computer providing access to the programs via a network transmission line, wireless transmission media, signals propagating through space, radio waves, infrared signals, etc.

Having described certain embodiments of methods and systems for displaying representations of facial expressions and activity indicators on devices, it will now become apparent to one of skill in the art that other embodiments incorporating the concepts of the disclosure may be used. Therefore, the disclosure should not be limited to certain embodiments, but rather should be limited only by the spirit and scope of the following claims.

What is claimed is:

1. A method for displaying representations of facial expressions on devices, the method comprising:
   receiving, by a processor on a device, data from a sensor coupled to the device;
   identifying, by the processor, responsive to the received data, a level of progress that a user of the device made towards a goal;
   selecting, by the processor, responsive to the identification, an icon representing a facial expression; and
   modifying, by the processor, a level of power for each of a plurality of light indicators embedded in the device to display the icon by, for each light indicator of the plurality of light indicators;
   switching the each light indicator on and off multiple times; and
   controlling an on-time of the each light indiactor using pulse width modulation.

2. The method of claim 1 further comprising monitoring, by the sensor, at least one physical parameter of the user.

3. The method of claim 2 further comprising generating, by the sensor, data associated with the monitored at least one physical parameter.

4. The method of claim 3 further comprising transmitting, by the sensor, to the processor, the generated data.

5. The method of claim 1 further comprising determining that the user has made progress towards completing a goal, responsive to the received data.

6. The method of claim 1 further comprising determining that the user has not made progress towards completing a goal, responsive to the received data.

7. The method of claim 1, wherein identifying further comprises comparing the received data with a threshold associated with the goal.

8. The method of claim 1, wherein selecting further comprises selecting the icon to provide feedback to the user regarding the level of progress.

9. The method of claim 1, wherein the modifying the level of power for each of the plurality of light indicators creates a pattern of lights on the device, the pattern of lights representing the facial expression.

10. A system comprising a memory and a processor, the system operable to perform a method comprising:
    receiving data from a sensor coupled to a device;
    identifying, responsive to the received data, a level of progress that a user of the device made towards a goal;
    selecting, responsive to the identification, an icon representing a facial expression; and
    modifying a level of power for each of a plurality of light indicators embedded in the device to display the icon by, for each light indicator of the plurality of light indicators, modifying a drive current of a microcontroller output, the microcontroller output configured to control the level of power available to the each light indicator.

11. The system of claim 10, wherein the device further comprises a personal fitness device.

12. The system of claim 10, wherein the sensor further comprises means for determining a physical parameter associated with the user.

13. The system of claim 10, wherein selecting further comprises:
    retrieving, from a data store, an identification of the icon based on an association between the icon and the level of progress.

14. A method for displaying a representation of a type of activity monitored by a device, the method comprising:
    receiving, by a processor on a device, data from a sensor coupled to the device;
    identifying, by the processor, responsive to the received data, a type of activity of a user of the device;
    selecting, by the processor, responsive to the identification, at least one icon representing the type of activity; and
    modifying, by the processor, a level of power for each of a plurality of light indicators embedded in the device to display the icon by, for each light indicator of the plurality of light indicators, modifying a drive current of a microcontroller output, the microcontroller output configured to control the level of power available to the each light indicator.

15. The method of claim 14 wherein identifying further comprises determining, by the processor, responsive to accelerometer data included in the received data, that a level of acceleration of the user is associated with one of a plurality of activities.

16. The method of claim 14 wherein identifying further comprises determining, by the processor, responsive to a motion signature included in the received data, that a level of acceleration of the user is associated with one of a plurality of activities.

17. A method for displaying a representation of a type of activity monitored by a device, the method comprising:
    receiving, by a processor on a device, from a user of the device, an identification of a type of activity undertaken by the user;
    selecting, by the processor, responsive to the identification, at least one icon representing the type of activity; and
    modifying, by the processor, a level of power for each of a plurality of light indicators embedded in the device to display the icon by, for each light indicator of the plurality of light indicators:
    switching the each light indicator on and off multiple times; and
    controlling an on-time of the each light indicator using pulse width modulation.

\* \* \* \* \*